(12) United States Patent
Mukkamala et al.

(10) Patent No.: US 10,398,323 B2
(45) Date of Patent: *Sep. 3, 2019

(54) METHODS AND APPARATUS FOR DETERMINING PULSE TRANSIT TIME AS A FUNCTION OF BLOOD PRESSURE

(71) Applicant: Board of Trustees of Michigan State University, East Lansing, MI (US)

(72) Inventors: Ramakrishna Mukkamala, Okemos, MI (US); Mingwu Gao, East Lansing, MI (US)

(73) Assignee: Board of Trustees of Michigan State University, East Lansing, MI (US)

( * ) Notice: Subject to any disclaimer, the term of this patent is extended or adjusted under 35 U.S.C. 154(b) by 1432 days.

This patent is subject to a terminal disclaimer.

(21) Appl. No.: 14/011,063

(22) Filed: Aug. 27, 2013

(65) Prior Publication Data

US 2014/0066788 A1 Mar. 6, 2014

Related U.S. Application Data

(60) Provisional application No. 61/693,808, filed on Aug. 28, 2012.

(51) Int. Cl.
*A61B 5/021* (2006.01)
(52) U.S. Cl.
CPC ................. *A61B 5/02125* (2013.01)
(58) Field of Classification Search
None
See application file for complete search history.

(56) References Cited

U.S. PATENT DOCUMENTS 5,241,964 A * 9/1993 McQuilkin ........ A61B 5/02125
600/485
5,503,156 A * 4/1996 Millar .................... A61B 5/021
600/485

(Continued)

FOREIGN PATENT DOCUMENTS

EP 0443267 A1 * 8/1991 ......... A61B 5/02125
WO WO2012/021765 2/2012

OTHER PUBLICATIONS

Solberg, Lars Erik, Ilangko Balasingham, and Svein-Erik Hamran. "Candidate estimators for aorta diameter estimation using monostatic radar." 2010, Proceedings of the Fifth International Conference on Body Area Networks. ACM, p. 124-130.*

(Continued)

*Primary Examiner* — Patricia Mallari
*Assistant Examiner* — Jairo H Portillo
(74) *Attorney, Agent, or Firm* — Harness, Dickey & Pierce, PLC

(57) ABSTRACT

A method is provided for determining pulse transit time of a subject as a function of blood pressure. The method includes: measuring a proximal waveform indicative of the arterial pulse at a proximal site of the subject; measuring a distal waveform indicative of the arterial pulse at a distal site of the subject; defining a relationship between the proximal waveform and the distal waveform in terms of unknown parameters of a nonlinear model; determining the unknown parameters of the nonlinear model from the measured proximal waveform and the measured distal waveform; and determining pulse transit time for the subject as a function of blood pressure from the parameters of the nonlinear model. The nonlinear model can account for arterial compliance and peripheral wave reflection, where the arterial compliance depends on blood pressure.

18 Claims, 4 Drawing Sheets

Nonlinear Tube-Load Model

(56) References Cited

U.S. PATENT DOCUMENTS

| | | | |
|---|---|---|---|
| 6,129,674 A * | 10/2000 | Ovadia-Blechman | A61B 5/026 600/481 |
| 6,740,045 B2 | 5/2004 | Amano | |
| 8,313,439 B2 | 11/2012 | McCombie et al. | |
| 2006/0149152 A1 * | 7/2006 | Amitzur | A61B 5/02007 600/485 |
| 2006/0224073 A1 * | 10/2006 | Lin | A61B 5/02007 600/513 |
| 2007/0038090 A1 * | 2/2007 | Moon | A61B 8/08 600/437 |
| 2009/0287097 A1 | 11/2009 | Lowe | |
| 2010/0016736 A1 * | 1/2010 | Hahn | G06K 9/00496 600/485 |
| 2010/0241011 A1 * | 9/2010 | McCombie | A61B 5/02125 600/485 |
| 2011/0263989 A1 | 10/2011 | Mukkamala et al. | |
| 2011/0270098 A1 | 11/2011 | Chowienczyk et al. | |

OTHER PUBLICATIONS

Hahn, Jin-Oh, et al. "A new approach to reconstruction of central aortic blood pressure using "Adaptive" transfer function." 2008, Engineering in Medicine and Biology Society, 2008. EMBS 2008. 30th Annual International Conference of the IEEE, p. 813-816.*

Zhang, Qiao, et al. "Pulse transit time-based blood pressure estimation using hilbert-huang transform.", 2009, Engineering in Medicine and Biology Society, 2009. EMBC 2009. Annual International Conference of the IEEE, p. 1785-1788.*

Xu, Da, et al. "Monitoring aortic stiffness in the presence of measurement artifact based on an arterial tube model.", 2010 Engineering in Medicine and Biology Society (EMBC), 2010 Annual International Conference of the IEEE, p. 3453-3456.*

Francis, Said Elias. Continuous estimation of cardiac output and arterial resistance from arterial blood pressure using a third-order windkessel model. Diss. Massachusetts Institute of Technology, 2007.*

Sugimachi, Masaru, et al. "A new model-based method of reconstructing central aortic pressure from peripheral arterial pressure." The Japanese journal of physiology 51.2 (2001): 217-222.*

Xu, Ke, Mark Butlin, and Alberto P. Avolio. "Effects of pressure-dependent segmental arterial compliance and postural changes on pulse wave transmission in an arterial model of the human upper limb." Engineering in Medicine and Biology Society, EMBC, 2011 Annual International Conference of the IEEE. IEEE, 2011.*

Y. Chiu et al., "Determination of Pulse Wave Velocities With Computerized Algorithms", American Heart Journal, vol. 121, No. 5, pp. 1460-1470 (1991).

J. Sola et al., "Parametric Estimation of Pulse Arrival Time: A Robust Approach to Pulse Wave Velocity", Physiological Measurement, vol. 30, No. 7, pp. 603-615, (2009).

J. Sola et al., "Non-Invasive and Non-Occlusive Blood Pressure Estimation Via a Chest Sensor", accepted for publication in future issue, IEEE (2013).

J. Pruett, et al., "Measurement of Pulse-Wave Velocity Using a Beat-Sampling Technique", Annals of Biomedical Engineering, vol. 16, No. 4, pp. 341-347, (1988).

D. Xu, et al., "Improved Pulse Transit Time Estimation by System Identification Analysis of Proximal and Distal Arterial Waveforms", American Journal of Physiology, pp. 1389-1395, (2011).

G. Zhang et al., "Robust, Beat-To-Beat Estimation of the True Pulse Transit Time From Central and Peripheral Blood Pressure or Flow Waveforms Using an Arterial Tube-Load Model", 2011 Annual International Conference of the IEEE Engineering in Medicine and Biology Society, vol. 2011, pp. 4291-4294 (2011).

* cited by examiner

METHODS AND APPARATUS FOR DETERMINING PULSE TRANSIT TIME AS A FUNCTION OF BLOOD PRESSURE

CROSS-REFERENCE TO RELATED APPLICATIONS

This application claims the benefit of U.S. Provisional Application No. 61/693,808, filed on Aug. 28, 2012. The entire disclosure of the above application is incorporated herein by reference.

GOVERNMENT RIGHTS

This invention was made with government support under 0643477 awarded by the National Science Foundation and under W81XWH-11-2-0016 awarded by the U.S. Army. The government has certain rights in the invention.

FIELD

The present disclosure relates to methods and apparatus for determining pulse transit time (PTT) as a function of blood pressure (BP) without inducing an artificial BP change.

BACKGROUND

This section provides background information related to the present disclosure which is not necessarily prior art.

PTT is the time delay for the energy wave to travel between two sites in the arteries. According to the Bramwell-Hill equation, PTT varies with the arterial compliance (i.e., $PTT=\sqrt{(LC)}$, where L is the arterial inertance and C is the arterial compliance). PTT indeed decreases as the arteries stiffen with aging and disease. Further, PTT often shows a tight relationship with BP. The physiologic mechanism for this relationship is well understood. The arterial compliance decreases as BP increases, because collagen fibers are slack and do not apply tension until the arterial wall is stretched. PTT, in turn, decreases due to the Bramwell-Hill equation. While changes in vasomotor tone can also acutely modulate the arterial compliance, this effect is less of a factor in the aorta wherein smooth muscle is relatively sparse.

PTT can be estimated simply from the relative timing between proximal and distal waveforms indicative of the arterial pulse. Hence, PTT has (a) proven to be a convenient marker of arterial stiffness and (b) could conceivably permit continuous, non-invasive, and cuff-less BP monitoring in the acute setting and even over longer time periods (e.g., months to a few years) as the impact of aging and disease on the arteries are slow processes.

The conventional PTT estimation technique is to detect the foot-to-foot time delay between the proximal and distal waveforms. The premise is that arterial wave reflection interference is negligible during late diastole and early systole when the waveform feet occur. By contrast, the reflected wave is often prominent by late systole. So, the peak-to-peak time-delay between the two waveforms typically does not provide a useful PTT estimate. Hence, by virtue of being estimated at the waveform feet, conventionally estimated PTT is precisely a marker of arterial stiffness at the level of diastolic BP and generally correlates best with diastolic BP.

However, wave reflection interference may not always be negligible at the waveform feet, particularly as heart rate changes and peripheral resistance increases. Just as important, since the foot-to-foot detection technique restricts its analysis to one pair of waveform samples, it is not robust to motion and other common artifact in the waveforms. Hence, this technique yields imperfect PTT estimates. Even seemingly small errors are problematic, as PTT itself is small. Compounding matters, BP changes perturb PTT relatively little. As a result, plots of diastolic BP versus foot-to-foot PTT often show significant scatter about the line of best fit. This scatter obviously limits the ability of PTT to track BP.

Several techniques have been proposed to improve the estimation of PTT from the same waveforms. These techniques have been shown or could reduce the scatter in BP versus PTT plots.

Some of the techniques analyze multiple systolic samples of the waveforms to obtain a PTT estimate at a BP level somewhere between diastolic and mean BP (rather than at diastolic BP). One such technique fits a line through the early systolic samples of each waveform and then finds the time of its intersection with the horizontal line passing through the minimum BP to establish PTT. Another technique fits a hyperbolic tangent model to the entire systolic upstroke of at least one of the waveforms and then uses the time of the model inflection point(s) to arrive at PTT. A third technique effectively averages multiple time delays taken from the early to mid-systolic samples of the two waveforms to determine PTT. By analyzing additional waveform samples, these techniques are more robust to artifact. However, wave reflection interference becomes a greater factor as the cardiac cycle progresses.

Other techniques analyze the entire waveforms to arrive at a PTT estimate at likely mean BP. One such technique represents the relationship between the proximal and distal waveforms with a linear black-box (i.e., not physically based) model that assumes arterial compliance is independent of BP. Then, the impulse response that optimally couples the proximal waveform to the distal waveform is identified. Finally, the time delay of the impulse response is detected as the PTT. Since the impulse response represents the distal arterial response to a very narrow pulse applied at the proximal artery at time zero, this PTT estimate is not corrupted by wave reflection. Another technique represents the relationship between the proximal and distal waveforms with a linear physical model that likewise assumes that the arterial compliance is independent of BP and accounts for wave reflection from the periphery, which is typically the dominant impedance mismatch site. Then, all parameters of the model, which include the true PTT (i.e., PTT in absence of wave reflection), are estimated by optimally coupling the waveforms. Hence, both of these linear model-based techniques provide an artifact robust estimate of the true PTT.

Although a number of PTT estimation techniques have been conceived, all yield one PTT estimate at a single BP level. It would be desirable to have a technique that is able to estimate PTT as a function of BP (e.g., PTT for each and every BP level in the cardiac cycle). Such a technique would have at least three important patient monitoring applications.

One application is improved monitoring of arterial stiffness. In particular, the desired technique could be used to correct PTT for BP and thereby afford more meaningful tracking of arterial stiffness over time within a subject or more meaningful comparisons of arterial stiffness amongst different subjects.

Another application is calibrating PTT (in units of sec) to BP (in units of mmHg). To achieve this calibration, a subject-specific curve that relates PTT to BP (i.e., PTT as a function of BP) is needed. The conventional approach for constructing the curve is to measure both PTT and BP in a subject during an experimental perturbation that varies BP over a significant range such as vasoactive drug infusions. (BP could then be subsequently measured in that subject from only PTT by invoking the calibration curve.) However, the need for an experimental perturbation makes this approach less practical. The desired technique would provide the requisite curve without the need for inducing an artificial BP change (i.e., a "perturbationless calibration" approach).

A third application is tracking systolic BP via PTT. All of the previous techniques estimate PTT at BP levels between diastolic and mean BP and are thus best suited to track these BP values. The desired technique would afford a PTT estimate at systolic BP and thereby better track this BP value.

The background description provided herein is for the purpose of generally presenting the context of the invention. Work of the presently named inventors, to the extent it is described in this background section, as well as aspects of the description that may not otherwise qualify as prior art at the time of filing, are neither expressly nor impliedly admitted as prior art against the present invention.

SUMMARY

This section provides a general summary of the disclosure, and is not a comprehensive disclosure of its full scope or all of its features.

A method is provided for determining pulse transit time of a subject as a function of blood pressure. The method includes: measuring a proximal waveform indicative of the arterial pulse at a proximal site of the subject; measuring a distal waveform indicative of the arterial pulse at a distal site of the subject; defining a relationship between the proximal waveform and the distal waveform in terms of unknown parameters of a nonlinear model; determining the unknown parameters of the nonlinear model from the measured proximal waveform and the measured distal waveform; and determining PTT for the subject as a function of BP from the parameters of the nonlinear model. The nonlinear model can account for arterial compliance and peripheral wave reflection, where the arterial compliance depends on BP.

One exemplary embodiment of the method involves the measurement of BP waveforms and the use of a nonlinear physical model of the arteries. This method includes: measuring proximal and distal BP waveforms from the subject; defining a relationship between the waveforms in terms of unknown parameters of a nonlinear tube-load model that accounts for both the BP-dependent arterial compliance and peripheral wave reflection; estimating the unknown model parameters from the waveforms; and using the estimated parameters to specify PTT as a function of BP for the subject.

Further areas of applicability will become apparent from the description provided herein. The description and specific examples in this summary are intended for purposes of illustration only and are not intended to limit the scope of the present disclosure.

DRAWINGS

The drawings described herein are for illustrative purposes only of selected embodiments and not all possible implementations. They are not intended to limit the scope of the present disclosure.

The present invention will become more fully understood from the detailed description and the accompanying drawings, wherein.

Corresponding reference numerals indicate corresponding parts throughout the several views of the drawings.

DETAILED DESCRIPTION

Example embodiments will now be described more fully with reference to the accompanying drawings.

Figure 1:
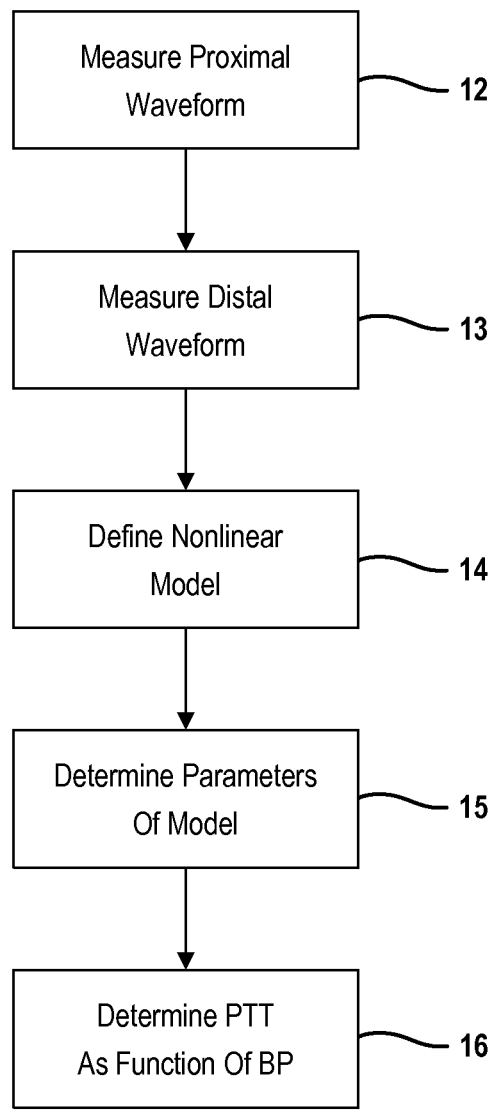
FIG. 1 is a flowchart depicting an example method for determining PTT of a subject as a function of BP.

FIG. 1 is a diagram depicting an example method for determining pulse transit time (PTT) for a subject as a function of blood pressure (BP). The present disclosure encompasses the recognition that PTT as a function of BP can be estimated from proximal and distal waveforms based on a nonlinear model that accounts for the BP-dependent arterial compliance as well as peripheral wave reflection. In this way, the true PTT at multiple BP levels is determined from the natural pulsatile variation in BP (nominally from about 80 to 120 mmHg) rather than through induction of an artificial BP change. The PTT-BP curve could not only be used for more convenient calibration of PTT to BP but also for more precise arterial stiffness monitoring and more accurate tracking of systolic BP via PTT.

First, the proximal waveform and the distal waveform are measured at 12 and 13, respectively. These waveforms may be obtained from various pairs of arterial sites, such as the carotid and femoral arteries. The waveforms can represent BP, blood velocity, blood volume, or any other variable indicative of the arterial pulse. The waveforms are measured using any of available methods including but not limited to catheterization, electrocardiography, tonometry, finger-cuff photoplethysmography, oscillometry at a constant cuff pressure, ultrasound, ballistocardiography, electrical bioimpedance, and pulse oximetry.

The waveforms are measured either simultaneously or sequentially while an ECG is continuously obtained. In the event that neither measured waveform represents BP, systolic, mean, and diastolic BP are also measured, for example with a standard cuff. One, both, or even none of the waveforms may then be calibrated with these BP values. For example, a blood volume waveform is calibrated so that its mean and peak-to-peak amplitude respectively equal mean BP and systolic BP minus diastolic BP.

Second, the relationship between the two waveforms is defined at 14 with an arterial model that is nonlinear at least in the sense of accounting for the BP-dependent arterial compliance while also accounting for peripheral wave reflection and perhaps other impedance mismatch sites. The model is preferably characterized by a small number of parameters so that it can be reliably identified from the limited information present in the measured waveforms. In one example, the model may be defined as a physical model. That is, the physical model is a frictionless tube with BP-dependent arterial compliance and a terminal load, where the tube represents the wave travel path between the proximal site and the distal site. In another example, the model may be a black-box model. An example of a black-box model is a nonlinear autoregressive exogenous input (ARX) or an output error (OE) structure whose parameters are dependent on BP or the amplitude of at least one waveform in the event that neither is a BP waveform or a waveform calibrated to BP. Other types of nonlinear models fall within the scope of this disclosure. It is also envisioned that the broader aspects of this disclosure can be extended to non-parametric models as well.

Third, the nonlinear model is identified at 15 by analysis of the pair of waveforms. For example, the parameters of the model are estimated so as to predict one waveform from the other. In the case of sequential waveform measurements, first, the impulse responses relating the ECG to each waveform are identified. These two impulse responses represent the proximal and distal waveforms in response to the same cardiac excitation (i.e., one average heartbeat) rather than sequential cardiac contractions. Then, the nonlinear model is identified by analysis of the impulse responses instead of the waveforms. For example, the model parameters are estimated so as to predict one impulse response from the other. In either the case of simultaneous or sequential waveform measurements, any tool known in the area of system identification can be employed to determine the nonlinear model including standard and total least squares parameter estimation.

Finally, the model parameters are used at 16 to specify PTT as a function of BP. In the case of a nonlinear physical model, PTT as a function of BP may be defined directly in terms of the parameter estimates. In the case of a nonlinear black-box model in which at least one waveform is a BP waveform or has been calibrated to BP, the time delay of the nonlinear ARX or OE structure is determined at each BP level and then the time delay is plotted versus BP. In the case of a nonlinear black-box model in which both waveforms are not BP waveforms, the time delay of the nonlinear ARX or OE structure is determined at the minimum, mean, and peak amplitudes and then these time delays are respectively plotted versus diastolic, mean, and systolic BP measurements via a standard cuff.

In one example embodiment, proximal and distal BP waveforms are simultaneously measured. The waveforms may be non-invasively obtained, for example from the carotid and femoral or dorsal pedal arteries via tonometry.

Figure 2:
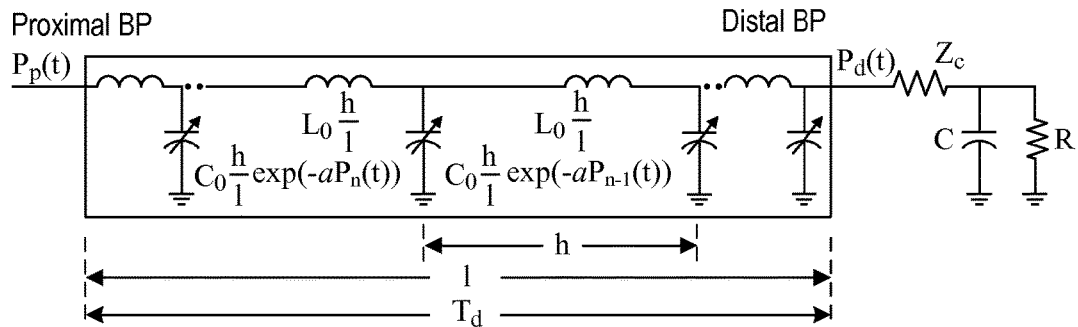
FIG. 2 is a diagram depicting a nonlinear tube-load model.

With reference to FIG. 2, the relationship between the proximal and distal BP waveforms ($P_p(t)$ and $P_d(t)$) is defined through a physical model. This example model is a nonlinear tube with a terminal load. The tube represents the large artery path for wave travel between the two measurement sites. The tube accounts for the large artery inertance ($L_O$), which is assumed to be constant, and the large artery compliance, which is dependent on BP. The large artery segmental compliance is specifically dependent on BP according to the following exponential relationship derived from experimental data:

$$C_0 \frac{h}{l} \exp(-\alpha P),$$

where l is the length of the tube, h is the segmental length, $C_0$ is the arterial compliance at zero BP, and $\alpha$ specifies the degree of nonlinearity. The terminal load represents the small arteries distal to the distal artery measurement site. The load accounts for peripheral resistance and compliance (R and C) while matching the average tube impedance at infinite frequency.

Figure 3:
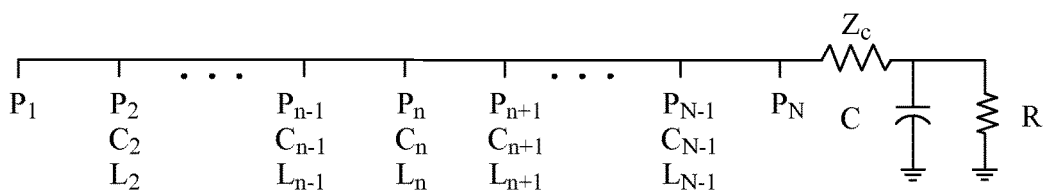
FIG. 3 is a diagram depicting a discretized nonlinear tube-load model.

Because the model is nonlinear, a finite difference method can be applied to its governing equations so as to predict $P_d(t)$ from $P_p(t)$. In particular, as shown in FIG. 3, the tube is discretized into N nodes. $P_1$ and $P_N$ correspond to $P_p(t)$ and $P_d(t)$, while $P_2$ thru $P_{N-1}$ represent BP at intermediate nodes along the tube. The compliance at each intermediate node n is $C_n = C_0/(N-2)\exp(-\alpha P_n)$, and the inertance at the node is $L_n = L_0/(N-2)$. Then, after also discretizing in time, $P_d(t)$ may be iteratively computed from $P_p(t)$ according to the following state-space equations:

$$\begin{bmatrix} P_1 \\ P_2 \\ P_3 \\ P_4 \\ P_5 \\ \vdots \\ P_{N-4} \\ P_{N-3} \\ P_{N-2} \\ P_{N-1} \end{bmatrix}^{k+1} = \begin{bmatrix} U^{k+1} \\ 0 \\ 0 \\ 0 \\ 0 \\ \vdots \\ 0 \\ 0 \\ 0 \\ 0 \end{bmatrix} + \quad (1)$$

$$\begin{bmatrix} 0 & 0 & \ddots & 0 & 0 \\ (N-2)^2 \Delta t^2 & (N-2)^2 \Delta t^2 & (N-2)^2 \Delta t^2 & & \\ \frac{\exp(\alpha P_2^k)}{K_1(1-\alpha P_2^k)} & 1-2\frac{\exp(\alpha P_2^k)}{K_1(1-\alpha P_2^k)} & \frac{\exp(\alpha P_2^k)}{K_1(1-\alpha P_2^k)} & \ddots & 0 \\ & (N-2)^2 \Delta t^2 & (N-2)^2 \Delta t^2 & (N-2)^2 \Delta t^2 & \\ 0 & \frac{\exp(\alpha P_3^k)}{K_1(1-\alpha P_3^k)} & 1-2\frac{\exp(\alpha P_3^k)}{K_1(1-\alpha P_3^k)} & \frac{\exp(\alpha P_3^k)}{K_1(1-\alpha P_3^k)} & \ddots \\ \vdots & \ddots & \ddots & \ddots & \vdots \\ & & (N-2)^2 \Delta t^2 & (N-2)^2 \Delta t^2 & (N-2)^2 \Delta t^2 \\ \ddots & \frac{\exp(\alpha P_{N-2}^k)}{K_1(1-\alpha P_{N-2}^k)} & 1-2\frac{\exp(\alpha P_{N-2}^k)}{K_1(1-\alpha P_{N-2}^k)} & \frac{\exp(\alpha P_{N-2}^k)}{K_1(1-\alpha P_{N-2}^k)} & 0 \\ & & (N-2)^2 \Delta t^2 & (N-2)^2 \Delta t^2 & (N-2)^2 \Delta t^2 \\ 0 & \ddots & \frac{\exp(\alpha P_{N-1}^k)}{K_1(1-\alpha P_{N-1}^k)} & 1-2\frac{\exp(\alpha P_{N-1}^k)}{K_1(1-\alpha P_{N-1}^k)} & \frac{\exp(\alpha P_{N-1}^k)}{K_1(1-\alpha P_{N-1}^k)} \end{bmatrix}$$

$$\begin{bmatrix} P_1 \\ P_2 \\ P_3 \\ P_4 \\ P_5 \\ \vdots \\ P_{N-3} \\ P_{N-2} \\ P_{N-1} \\ P_N \end{bmatrix}^k$$

$$P_N^{k+1} = \frac{\left[\frac{N-2}{\sqrt{K_1}\,K_2}\Delta t + \frac{N-2}{\sqrt{K_1}\,K_3}\Delta t + \frac{2(N-2)}{\sqrt{K_1}}\right]\sum_{i=1}^{k}(P_{N-1}^i - P_N^i) + \left[\frac{N-2}{\sqrt{K_1}\,K_2}\Delta t + \frac{N-2}{\sqrt{K_1}\,K_3}\Delta t - \frac{2(N-2)}{\sqrt{K_1}}\right]\sum_{i=1}^{k-1}(P_{N-1}^i - P_N^i) - \left[\frac{1}{K_3} - \frac{2}{\Delta t}\right]P_N^k}{\frac{1}{K_3} + \frac{2}{\Delta t}} \quad (2)$$

where the superscript k denotes the time index and $\Delta t$ is the time step. These equations have four unknown parameters, $K_1 = L_0 C_0$, $K_2 = Z_c C$, $K_3 = RC$ and $\alpha$.

The model parameters are estimated from the measured waveforms. First, a physiologic range of the four parameters is selected. Then, for each candidate set of parameters, $P_d(t)$ is predicted from $P_p(t)$ via equations (1) and (2) above. Finally, the candidate parameter set that yields the minimum mean squared error between the predicted and measured $P_d(t)$ is chosen as the parameter estimates. Other methods for determining the parameters of the nonlinear model from the waveforms are also contemplated by this disclosure.

Finally, PTT as a function of BP is determined from the estimated parameters. In particular, for a fixed BP, PTT and BP may be related through the model parameters as follows:

$$PTT = \sqrt{L_0 C_0 \exp(-\alpha P)}, \quad (3)$$

Figure 4:
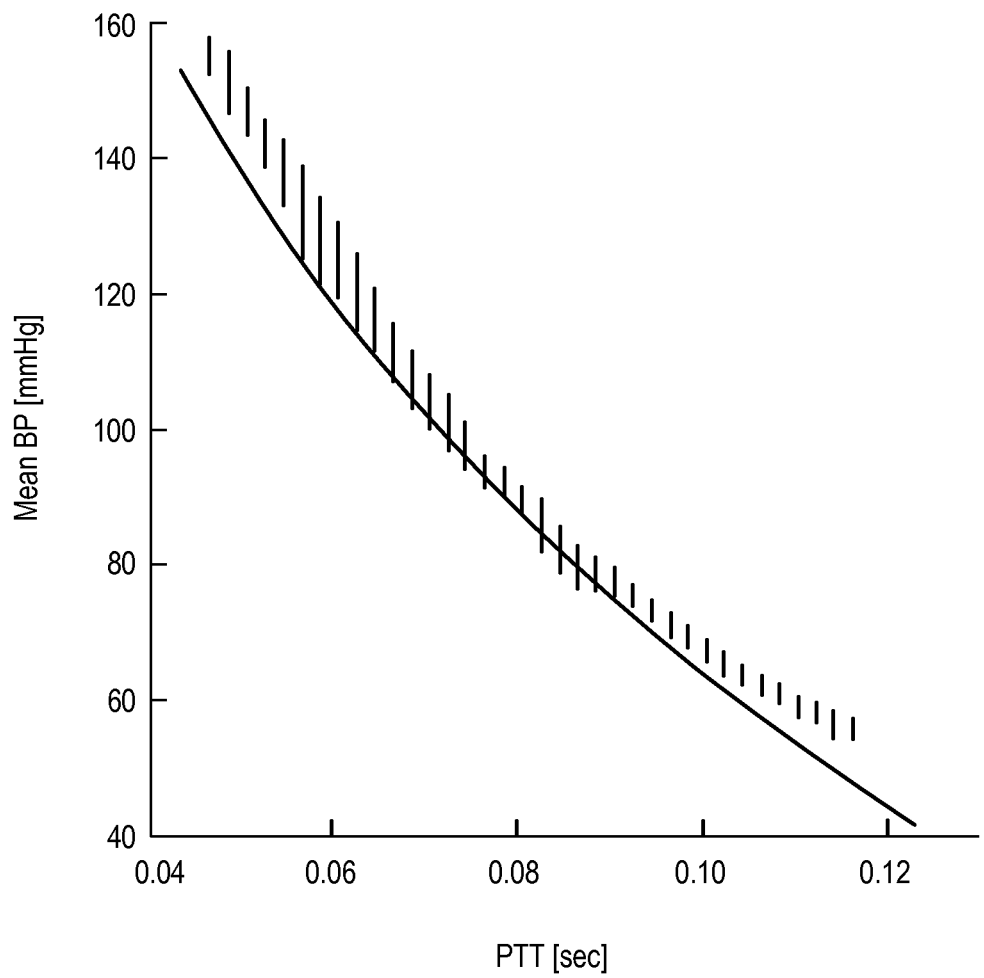
FIG. 4 is a graph of a calibration curve relating PTT to BP.

This equation with the estimated parameters yields PTT as a function of BP. FIG. 4 shows PTT as a function of BP derived by this nonlinear physical model-based approach. For comparison, the figure includes pairs of PTT estimated by a linear physical model-based technique (see Background) and measured mean BP (blue dots) during experimental interventions that changed BP (i.e., data not seen by the nonlinear approach). The derived PTT-BP function corresponded reasonably well to these reference data pairs.

The above embodiment can be refined in several ways. Some examples follow.

One of the measured waveforms can be a blood velocity waveform, and the measured waveforms can be measured at other arterial sites and with other sensors.

The large artery segmental compliance can depend on BP via various functions other than an exponential and on only time (rather than node (i.e., space) and time). Also, the time derivative of this compliance may be assumed to be negligible. The terminal load can be characterized by fewer parameters to, for example, only account for peripheral resistance or more parameters to, for example, also account for peripheral inertance.

Other finite difference and parameter estimation methods known in the art may instead be employed. Further, the number of unknown parameters for estimation can be reduced to three. First, the linear physical model-based technique is applied to the two waveforms and mean BP is determined to arrive at a single pair of PTT and BP. Then, this pair is substituted into equation (3) to make $L_0 C_0$ completely determined by $\alpha$.

Finally, PTT-BP functions other than equation (3) that are defined by the model parameters may possibly be employed.

The PTT-BP function obtained from the above embodiment could be used for more precise arterial stiffness monitoring. In this case, the distal BP waveform would preferably have been obtained from the femoral artery. In particular, PTT at a fixed BP level (e.g., 100 mmHg) could be used as the BP-corrected PTT value. This value is then divided into the distance between the measurement sites to arrive at a BP-corrected pulse wave velocity value.

Alternatively, the PTT-BP function could be used for more convenient calibration of PTT to BP. For example, in this case, the distal BP waveform would have been obtained from the dorsal pedal artery. The resulting calibration curve could then be used for subsequent cuff-less BP monitoring. First, proximal and distal blood volume waveforms are measured from an ear and toe via photoplethysmography. Second, PTT is estimated from the waveforms using a linear black-box model-based technique (see Background). Finally, this PTT is mapped through the calibration curve to arrive at an estimate of mean BP. The first two steps could also be performed immediately after construction of the calibration curve. In this way, the curve could be empirically adjusted to better accommodate the subsequent PTT estimates, which are from different arterial sites and sensors than those used to construct the curve. Since the curve will change over time due to aging and disease, it should be periodically updated (e.g., every few months to years) using the above embodiment. Other specific implementations and patient monitoring applications would be readily apparent to any one skilled in the art.

The techniques described herein may be implemented by one or more computer programs executed by one or more processors. The computer programs include processor-executable instructions that are stored on a non-transitory tangible computer readable medium. The computer programs may also include stored data. Non-limiting examples of the non-transitory tangible computer readable medium are nonvolatile memory, magnetic storage, and optical storage.

Some portions of the above description present the techniques described herein in terms of algorithms and symbolic representations of operations on information. These algorithmic descriptions and representations are the means used by those skilled in the data processing arts to most effectively convey the substance of their work to others skilled in the art. These operations, while described functionally or logically, are understood to be implemented by computer programs. Furthermore, it has also proven convenient at times to refer to these arrangements of operations as modules or by functional names, without loss of generality.

Unless specifically stated otherwise as apparent from the above discussion, it is appreciated that throughout the description, discussions utilizing terms such as "processing" or "computing" or "calculating" or "determining" or "displaying" or the like, refer to the action and processes of a computer system, or similar electronic computing device, that manipulates and transforms data represented as physical (electronic) quantities within the computer system memories or registers or other such information storage, transmission or display devices.

Certain aspects of the described techniques include process steps and instructions described herein in the form of an algorithm. It should be noted that the described process steps and instructions could be embodied in software, firmware or hardware, and when embodied in software, could be downloaded to reside on and be operated from different platforms used by real time network operating systems.

Figure 5:
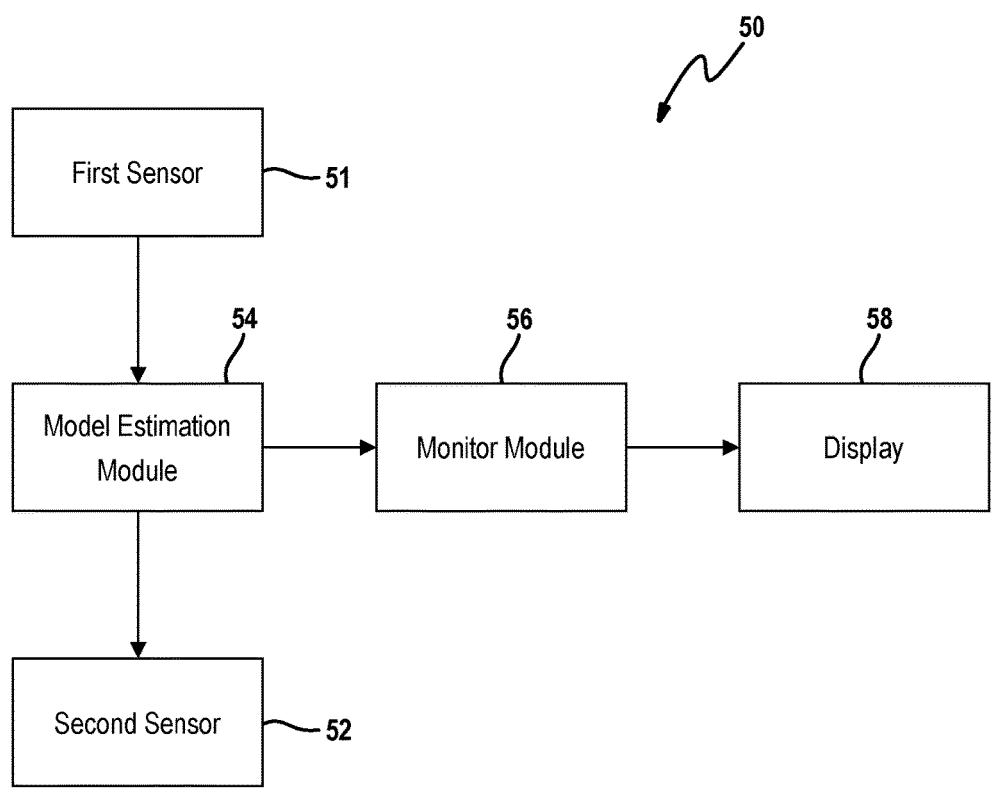
FIG. 5 is a diagram of an example system that implements methods for determining PTT as a function of BP.

FIG. 5 depicts an example computer-implemented system 50 that implements one or more of the methods described above. The system 50 is comprised generally of two or more sensors 51, 52, a parameter determination module 54, a diagnostic module 56 and at least one output device 58 such as a display. However, it can be appreciated that the system 50 may include more or less sensors and modules.

The first sensor 51 is configured to measure a waveform at a proximal arterial site of the subject; whereas, the second sensor 52 is configured to measure a waveform at a distal arterial site of the subject. For example, the first and second sensors may be further defined as an applanation tonometer for measuring BP of the subject. In another example, the first and second sensors 51, 52 may be further defined as pulse oximeters. It is readily understood that other types of sensors fall within the scope of this disclosure.

The model estimation model 54 determines the parameters of a nonlinear model that relates the proximal arterial waveform to the distal arterial waveform. To do so, the model estimation module 54 receives the measured waveforms from the first and second sensors 51, 52 and samples the waveforms. The model estimation module 54 then determines the parameters of the nonlinear model from the samples of the measured waveforms. The parameters are determined by implementing the various methods described above. In an exemplary embodiment, the nonlinear model is pre-configured in a data store of the system and thus accessible to the parameter determination module 54.

Given the determined parameter values of the model, the monitor module 56 can compute the PTT of the subject as a function of BP. This metric has important patient monitoring applications, such as those described above. In some embodiments, the monitor module 56 may monitor computed quantities and trigger alarms when monitored quantities exceed thresholds. In other embodiments, the monitor module 56 may administer therapy to the subject or modify the subject's therapy, based on the monitored quantities. Lastly, the monitor module 56 may interface with the display 58 to present the monitored quantities on the display 58. However, it can be appreciated that other types of output devices may be used in lieu of the display device.

This system 50 may be specially constructed for the required purposes, or it may comprise a general-purpose computer selectively activated or reconfigured by a computer program stored on a computer readable medium that can be accessed by the computer. Such a computer program may be stored in a tangible computer readable storage medium, such as, but not limited to, any type of disk including floppy disks, optical disks, CD-ROMs, magnetic-optical disks, read-only memories (ROMs), random access memories (RAMs), EPROMs, EEPROMs, magnetic or optical cards, application specific integrated circuits (ASICs), or any type of media suitable for storing electronic instructions, and each coupled to a computer system bus. Furthermore, the computers referred to in the specification may include a single processor or may be architectures employing multiple processor designs for increased computing capability. In other embodiments, the term module can refer to an application specific integrated circuit (ASIC), an electronic circuit, a combinational logic circuit, and/or other suitable components that provide the described functionality.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the disclosure, and all such modifications are intended to be included within the scope of the disclosure.

What is claimed is:

1. A method for determining pulse transit time as a function of blood pressure for a subject, comprising:
measuring a proximal waveform indicative of an arterial pulse at a proximal site of the subject using a first sensor;
measuring a distal waveform indicative of the arterial pulse at a distal site of the subject using a second sensor;
defining a relationship between the proximal waveform and the distal waveform in terms of unknown parameters of a nonlinear model, where the nonlinear model accounts for wave propagation and reflection and accounts for arterial compliance that depends on blood pressure, and where the unknown parameters define a function relating pulse transit time and blood pressure;
determining the unknown parameters of the nonlinear model from the measured proximal waveform and the measured distal waveform; and
determining pulse transit time as a function of blood pressure using the parameters of the nonlinear model, where the steps of determining the unknown parameters of the nonlinear model and determining pulse transit time are implemented by a computer processor of a computing device.

2. The method of claim 1 wherein at least one of the proximal waveform and the distal waveform is indicative of blood pressure.

3. The method of claim 1 wherein the nonlinear model is further defined as a frictionless tube with blood pressure-dependent arterial compliance and a terminal load, where the tube represents a wave travel path between the proximal site and the distal site.

4. The method of claim 3 wherein the terminal load of the model is characterized by average tube characteristic impedance and peripheral resistance and compliance.

5. The method of claim 1 wherein the blood pressure-dependent arterial compliance is defined as $$C_0 \frac{h}{l} \exp(-\alpha P)$$

where $l$ is length of the tube, $h$ is segmental length, $C_0$ is arterial compliance at zero blood pressure, $\alpha$ specifies degree of nonlinearity and $P$ is blood pressure.

6. The method of claim 5 further comprises determining pulse transit time for the subject as a function of blood pressure in accordance with $$PTT = \sqrt{L_0 C_0 \exp(-\alpha P)}$$

where $L_0$ is arterial inertance, $C_0$ is arterial compliance at zero blood pressure, α specifies degree of nonlinearity, and P is blood pressure.

7. The method of claim 1 wherein determining the unknown parameters further comprises estimating the unknown parameters by predicting one of the proximal or distal waveforms from the other waveform via a least squares search over a physiologic parameter range.

8. The method of claim 7 wherein predicting one of the proximal or distal waveforms from the other waveform further comprises using a finite difference method.

9. The method of claim 1 further comprises
measuring a proximal blood volume waveform indicative of blood volume at the proximal site of the subject;
measuring a distal blood volume waveform indicative of blood volume at the distal site of the subject;
determining pulse transit time at a single blood pressure from the measured proximal and distal blood volume waveforms; and
determining blood pressure from the determined pulse transit time using the function relating pulse transit time to blood pressure.

10. A method for determining pulse transit time as a function of blood pressure for a subject, comprising:
measuring a proximal waveform indicative of blood pressure at a proximal site of the subject using a first sensor;
measuring a distal waveform indicative of blood pressure at a distal site of the subject using a second sensor;
defining a relationship between the proximal waveform and the distal waveform in terms of unknown parameters of a nonlinear tube-load model, wherein the nonlinear tube-load model accounts for wave propagation and arterial compliance that depends on blood pressure;
determining the unknown parameters of the nonlinear model from the measured proximal waveform and the measured distal waveform; and
determining pulse transit time as a function of blood pressure from the determined parameters of the nonlinear tube-load model, where the steps of determining the unknown parameters of the nonlinear model and determining pulse transit time are implemented by a computer processor of a computing device.

11. The method of claim 10 further comprises measuring a proximal waveform from a carotid artery and measuring a distal waveform from a femoral artery.

12. The method of claim 10 wherein the nonlinear tube-load model includes a terminal load and the terminal load is characterized by peripheral resistance, compliance and average tube characteristic impedance.

13. The method of claim 10 wherein tube is frictionless and the blood pressure-dependent arterial compliance is defined as $$C_0 \frac{h}{l} \exp(-\alpha P)$$

where l is length of the tube, h is segmental length, $C_0$ is arterial compliance at zero blood pressure, α specifies degree of nonlinearity and P is blood pressure.

14. The method of claim 10 wherein determining the unknown parameters further comprises estimating the unknown parameters by predicting one of the proximal or distal waveforms from the other waveform via a least squares search over a physiologic parameter range.

15. The method of claim 14 wherein predicting one of the proximal or distal waveforms from the other waveform further comprises using a finite difference method.

16. The method of claim 10 further comprises determining pulse transit time for the subject as a function of blood pressure in accordance with $$PTT = \sqrt{L_0 C_0 \exp(-\alpha P)}$$

where $L_0$ is arterial inertance, $C_0$ is arterial compliance at zero blood pressure, α specifies degree of nonlinearity, and P is blood pressure.

17. The method of claim 10 further comprises
measuring a proximal blood volume waveform indicative of blood volume at the proximal site of the subject;
measuring a distal blood volume waveform indicative of blood volume at the distal site of the subject;
determining pulse transit time at a single blood pressure from the measured proximal and distal blood volume waveforms; and
determining blood pressure from the determined pulse transit time using the function relating pulse transit time to blood pressure.

18. A method for determining pulse transit time as a function of blood pressure for a subject, comprising:
measuring a proximal waveform indicative of an arterial pulse at a proximal site of the subject using a first sensor;
measuring a distal waveform indicative of the arterial pulse at a distal site of the subject using a second sensor;
defining a relationship between the proximal waveform and the distal waveform in terms of unknown parameters of a nonlinear model, wherein the nonlinear model accounts for wave propagation and arterial compliance that depends on blood pressure;
determining the unknown parameters of the nonlinear model by fitting the measured proximal waveform to the measured distal waveform; and
determining pulse transit time as a function of blood pressure from the parameters of the nonlinear model, where the steps of determining the unknown parameters of the nonlinear model and determining pulse transit time are implemented by a computer processor of a computing device.

* * * * *